United States Patent [19]
Thibeault

[11] Patent Number: 5,554,161
[45] Date of Patent: Sep. 10, 1996

[54] TICK REMOVAL TOOL

[76] Inventor: Larry K. Thibeault, 5 Heritage Cir., Brookline, N.H. 03033

[21] Appl. No.: 420,872

[22] Filed: Apr. 12, 1995

[51] Int. Cl.$^6$ ..................................................... A61B 17/50
[52] U.S. Cl. ........................ 606/131; 606/210; 606/138; 81/300; 30/324; 30/326
[58] Field of Search ..................... 606/131, 210, 606/138; 294/100; 254/18; 81/300, 304, 3.44, 3.45; 425/279, 280, 283, 276; 30/324, 326, 433, 431

[56] References Cited

U.S. PATENT DOCUMENTS

| | | | |
|---|---|---|---|
| D. 335,166 | 4/1993 | Johnston | D22/122 |
| 825,147 | 7/1906 | Mosteller | 425/283 |
| 4,213,460 | 7/1980 | Weiner | 606/131 |
| 4,303,268 | 12/1981 | Davidson | 294/16 |
| 4,938,764 | 7/1990 | Glaberson | 606/131 |
| 4,979,771 | 12/1990 | Childs, III | 294/99.2 |
| 5,078,729 | 1/1992 | Eichhorn | 606/210 |
| 5,116,347 | 5/1992 | Butler | 606/131 |
| 5,246,449 | 9/1993 | Webster | 606/131 |

Primary Examiner—Robert A. Hafer
Assistant Examiner—Justine Yu
Attorney, Agent, or Firm—Vernon C. Maine

[57] ABSTRACT

A tool for removing ticks and similar parasites. A spoon-shaped tool, the spoon of which is split lengthwise and hinged to rotate the split spoon sections normally open far enough to fit over a tick's body, then rotated closed into an overlapping relationship by thumb and forefinger closing pressure to trap the tick about the neck in a v-shaped slit in one side of the opening in the spoon. A mechanical stop prevents the slit from closing completely to sever the tick from it's head. The handle may have a centerline hinge, integral spring, and thumb and finger locators to facilitate use of the tool in a palm-down fashion by either hand. The spoon sections may have opposing slits that close upon each other to likewise trap the tick. The tick is at all times visible in the open bowl of the tool. The tool may be molded in one piece, with a "living hinge" and spring incorporated into it's design.

11 Claims, 2 Drawing Sheets

TICK REMOVAL TOOL

BACKGROUND OF THE INVENTION

1. Technical Field of the Invention

This invention most generally relates to means for removing ticks and similar parasites from living hosts.

More particularly, it relates to the manual removal from the host of live ticks whose head and jaws are embedded in the host.

2. Background Art

Ticks are members of a group of relatively large blood sucking insects of the order ACARI, and of the families IXODIDAE, ARGASIDAE and HIPPOBOSCIDAE. They are wingless and have a barbed proboscis which extends from the head. The proboscis is inserted into the skin of a warm blooded host for extracting blood, which is stored in the tick's large sac-like abdomen. When it's proboscis and head are firmly embedded in a host's skin, it is not easily removed. Rocky Mountain Spotted Fever and Lyme Disease are two examples of infectious agents which can be transmitted by these parasites.

Ticks have a well defined division between the head and thorax-abdomen. The latter is relatively easy to rend from the former when attempting to remove the tick from the host by twisting or pulling on the tick's plump body with fingers or tools, leaving the head and barbed proboscis inaccessibly embedded in the host. This can lead to further injury and increased likelyhood of infection.

The tick problem has prompted a wide-ranging response over the years. Many new patents have issued even recently, indicating recognition of a continuing problem and room for improvement in the field.

The overall scope of the art is broad, however the differences between individual disclosures are much less dramatic. Some of the art is directed to professionals who can justify more expensive equipment. Some can be seen to be cheaper, simpler, and more readily used by the casual user like parents, pet owners, farmers, and so on.

Among the background art is a small plastic spoon with a V slit in the tip opposite the handle, the slit oriented parallel to the handle, evidently used to engage the tick body in a forward motion and pry or scoop it off the skin with a shoveling or prying motion of the spoon. It makes no provision or suggestion for structure to trap the tick for examination and disposal, or for a more ergonomic grip and hand position for more sensitive manipulation. This device requires an awkward forearm motion or twisting wrist motion to manipulate the device.

There are electrified "zappers" like Johnston's U.S. design Pat. No. D335,166, Apr. 27, 1993, but these devices are unnecessarily heavy, bulky, costly and perhaps intimidating or even painful to use. They likewise make little or no attempt to optimize the shape and grip for the sensitivity of the task.

Eichhorn, U.S. Pat. No. 5,078,729, Jan. 7, 1992, discloses a spring-loaded, normally closed, squeeze clamp where the jaws, when closed, form a cavity of sufficient size to contain the tick's body, with a small opening in the cavity at the extreme end of the closed jaws to prevent the crushing and severing of the tick's body at the point of penetration in the host's skin. The clamp is held in the open position, vertically aligned and positioned over the tick and allowed to close on the tick, enabling the user to then twist or pull to extract the tick from the host. This device utilizes a normally closed clamping action, and obscures the tick from the user's view during the critical extraction process. It requires an inordinate amount of arm and wrist motion to position and operate.

Tweezers and modified tweezers are illustrated by Davidson, U.S. Pat. No. 4,303,268, Dec. 1, 1981. This device may be best described as a bootie on a pair of tweezers. It is simply a retention means to hold a pair of common tweezers in closing tension against a tick's body. The axis of application and operation is straight down on the target, and interferes with the line of sight. There is no provision to prevent inadvertent crushing of the tick, and the operation of such a device is likely to induce excessive forces and movements relative to the necessary delicacy of the extraction process.

Childs, U.S. Pat. No. 4,979,771, Dec. 25, 1990, discloses a normally-open variation of Eichhorn with an electric heater which applies heat to the tick when the device is closed, to induce the tick to let go.

Glaberson, U.S. Pat. No. 4,938,764, Jul. 3, 1990, discloses a simple handle and wire loop with a narrow section; the large opening of the loop positioned over the tick and pulled back to bring the narrow section of the loop around the tick's neck. No moving parts, but it does not fully encircle the tick, and may not hold the tick securely after retraction, or the tick body if severed.

Huffman, U.S. Pat. No. 5,276,306, Jan. 4, 1994, discloses a heated tip and spoon combination, where the user relies on the heat to induce the tick to disengage, and then uses the spoon to scoop up and remove the tick.

Webster, U.S. Pat. No. 5,246,449, Sep. 21, 1993, discloses two prying, lifting, leveraging devices. One is an arm with a forked end that is engaged laterally around the tick's neck, and has a hinged lifting lever that when actuated presses downward against the host's skin to apply a lifting force on the fork and the tick.

The other means illustrated is an addition to a common staple puller, where the outer edge of one jaw of the puller is equipped with a base plate configured with a keyhole slot, the narrowest point still sufficiently wide to pass around the neck of the tick, the central opening large enough to pass the tick's head.

A second plate is attached to the inner, curved edge of the opposing jaw of the staple puller, and is slotted so as at and during the closing of the staple puller, it will engage the tick about the neck and pry the tick upward, pulling the tick's head through the opening in the base plate. The tick's head should pass through the base plate as the tick is extracted.

Butler, U.S. Pat. No. 5,116,347, May 26, 1992, discloses an enhanced, pliers-type of handtool. The handle of the one-handed device is perpendicular to the line of sight. The cavity in operation forms an open bowl, providing a clear view of the tick and the extraction process. The jaws of the pliers have beveled mating edges, as well as mechanical stops to provide the optimal opening for the tick's neck.

The principle advantage of a pliers-type tool is the increased pinching force afforded at the jaws by the leverage of the plier handles. This is not a requirement in this application, and in fact teaches away from the sensitivity required for this task.

A further disadvantage to a pliers type tool for this application is that it requires the back end of the hand, the second, third and forth digits opposing the heel of the hand, to open and close a disporportionate distance compared to the limited travel between the thumb and forefinger and the limited force required for this application. This unnecessary muscle flexure and movement only increases the likelyhood of rending the tick's body from it's head.

It is common knowledge, and expounded in the art, that there is both risk and harm in severing or rendering the tick from it's head during attempts to remove it. Divergent ideas on manual removal of a live tick, intact, are all too readily apparent in the cited art. No solution in the art stands out as significantly better than other known solutions, but small variations have been recognized as patentable.

The actual removal of a live tick being a delicate matter, the most notable shortcoming of the art is a lack of recognition of the ergonomic benefits and improved performance achievable through design innovations that combine the sensitivity available in natural hand placement and thumb and finger movement, with complimentary structure that is a task-specific extension of the user's hand.

SUMMARY OF THE INVENTION

The main purpose of the tool is to provide a simple means for removing, intact, a tick or similar parasite which has it's head and jaws embedded in the skin of a host animal or person.

One object of the invention is to provide a handtool that employs a natural, palm-down, hand position and gripping motion closely simulating the motions that might be used to do the job with one's own fingers. A related objective is to be able to manipulate the tool with one hand without excessive arm or wrist motion, while maintaining a substantially unobstructed view of the tick.

To this end the invention may consist of a handle connected to two spoon-shaped sections which are hinged on an axis parallel to the handle so that they can be rotated from an open position where the bottom of the bowl of the spoon is cracked open for positioning over a tick or similar imbedded parasite, to a closed position where the spoon sections rotate towards and overlap each other to a small extent, by a simple pinching motion of the thumb and forefinger. The top of the bowl remains open, providing full visibility of the contents.

Another object of the invention is to inhibit the accidental severing of the tick's body from it's embedded head by over-rotation of spoon sections, while insuring enough closure to provide an adequate bearing surface or shoulder to exert upward pressure on the tick's body for removal.

To this end, either or both of the spoon sections may have a slit or irregular shape in it's leading edge, and a mechanical stop between rotational elements configured so that the tool can be positioned and closed to an overlapping position to the extend of it's mechanical stop, without severing the tick from it's head, due to the size of the remaining opening which is just sufficient to accommodate the neck of the tick.

Still another object is to maintain the spoon sections of the tool in a normally open condition so that actuation pressure is necessarily applied only at the time of engaging and removing the tick. To this end, the tool may be configured with a spring mechanism for holding the tool in a normally open position, and providing light resistance to any effort to rotate the spoon sections closed.

Still yet another object is to provide a thin edge structure at the point of engagement with the tick's neck, in order to readily fit between the surface of the host's skin and the tick's swollen torso. To this end, the wall of the slit or irregular shape in the leading edge, as well as the leading edge itself, may be tapered to present a thin interfacing edge to the forward or leading edge of the other spoon section.

A further object is to provide a bi-dextrous tool, readily grasped and manipulated by either hand. To this end, locators are provided on opposing sides of the handle interchangeably suitable for thumb and forefinger positioning and actuation.

A still further object of the invention is to minimize parts count and assembly in manufacturing. To this end the tool may be molded as a single piece tool with a so-called "living hinge" and an integral spring function, or as a one piece unit with a separate spring which is then attached or installed to complete the tool.

Still other objects and advantages of the present invention will become readily apparent to those skilled in this art from the following detailed description, wherein I have shown and described only a preferred embodiment of the invention, simply by way of illustration of the best mode contemplated by me on carrying out my invention. As will be realized, the invention is capable of other and different embodiments, and its several details are capable of modifications in various obvious respects, all without departing from the invention.

The objects and advantages of the invention may be further realized and attained by means of the instrumentalities and combinations particularly pointed out in the appended claims. Accordingly, the drawing and description are to be regarded as illustrative in nature, and not as restrictive.

DESCRIPTION OF THE PREFERRED EMBODIMENT

To those skilled in the art, the invention admits of many variations. As an example, the tool may consist of a handle connected to two spoon-shaped sections which are hinged on an axis parallel to the handle so that they can be rotated from an open position where the bowl of the spoon is open for positioning over a tick or similar imbedded parasite, to a closed position where the spoon sections overlap to a limited extent.

As a further example either or both of the spoon sections may have a slit or irregular shape in it's leading edge, configured so that the tool can be positioned and closed to an overlapping position to the extend of it's mechanical stop, and the size of the remaining opening is just sufficient to accommodate the neck of the tick. The wall and shoulder of the slit or opening will bear the tension exerted on the tick's body by the user.

As a yet further example, the tool may be configured with a spring or spring-like device for holding the tool in a normally open or closed position, and providing light resistance to any effort to rotate of the spoon sections to the opposite position.

As a still yet further example, the wall of the slit or irregular shape in the leading edge of the spoon section may be tapered to provide a thin interfacing edge to the forward or leading edge of the other spoon section, as the sections are closing, one overlapping the other.

As another example, the tool handle may be constructed or configured to have left and right side components which are attached to their respective spoon sections, and rotate with them.

As yet another example, the left and right side components of the two-component handle may have thumb and finger locators in opposing positions for a natural grip and use by either left or right handed users.

As still yet another example, the hinging mechanism of the rotating spoon sections may be a centerline hinge connecting the left and right side components of the handle.

As another further example, the spring may be installed in a spring recess in the handle.

As yet another further example, the tool may be made as a single piece molded tool with a "living hinge" and an integral spring function, or as a one piece unit with a separate spring which is then attached or installed to complete the tool.

Figure 1:
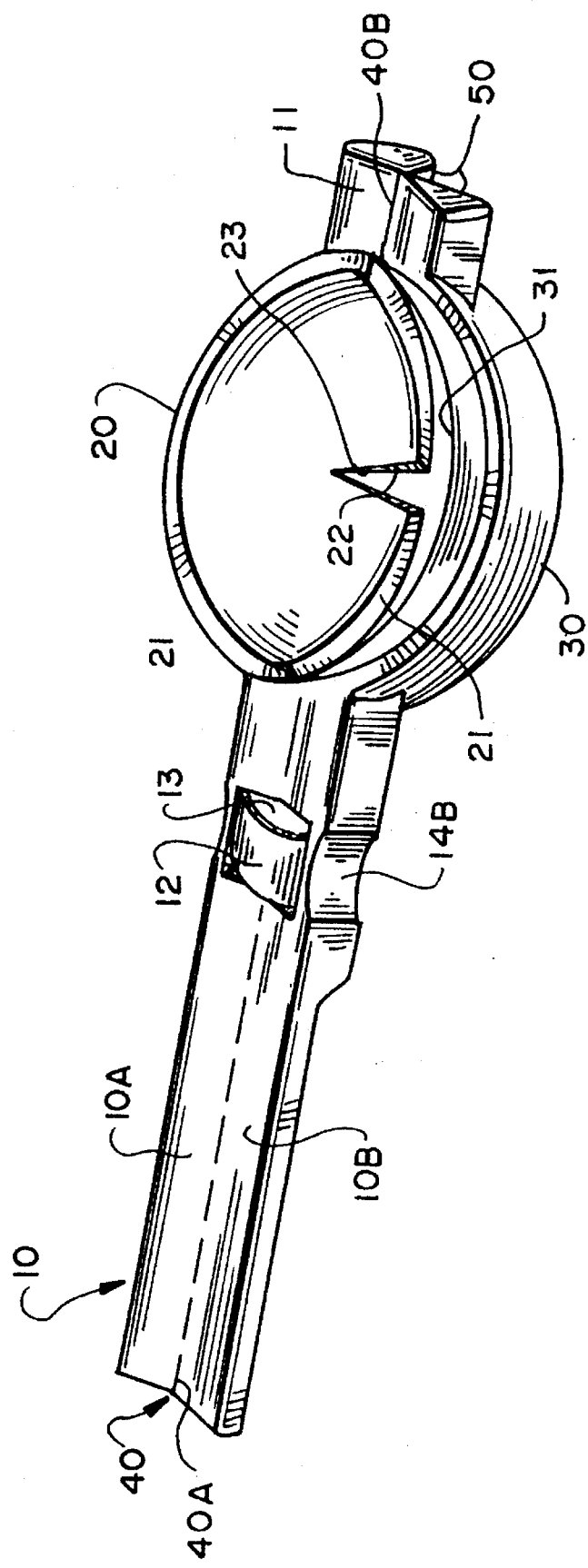
FIG. 1 is a perspective view of the preferred embodiment of the invention, showing the split handle and centerline hinge in the unflexed position and the spoon-shaped sections in the open position.
Figure 3:
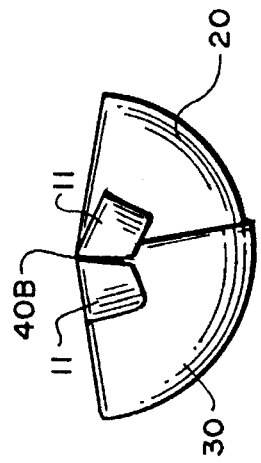
FIG. 3 is a spoon-end view of the embodiment of FIG. 1, with the spoon-shaped sections in the overlapping closed position.
Figure 2:
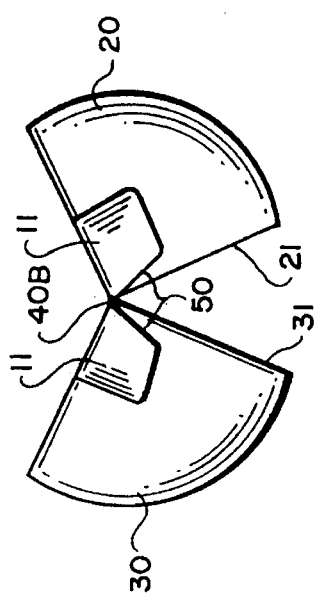
FIG. 2 is a spoon-end view of the embodiment of FIG. 1, with the spoon-shaped sections in the open position.
Figure 4:
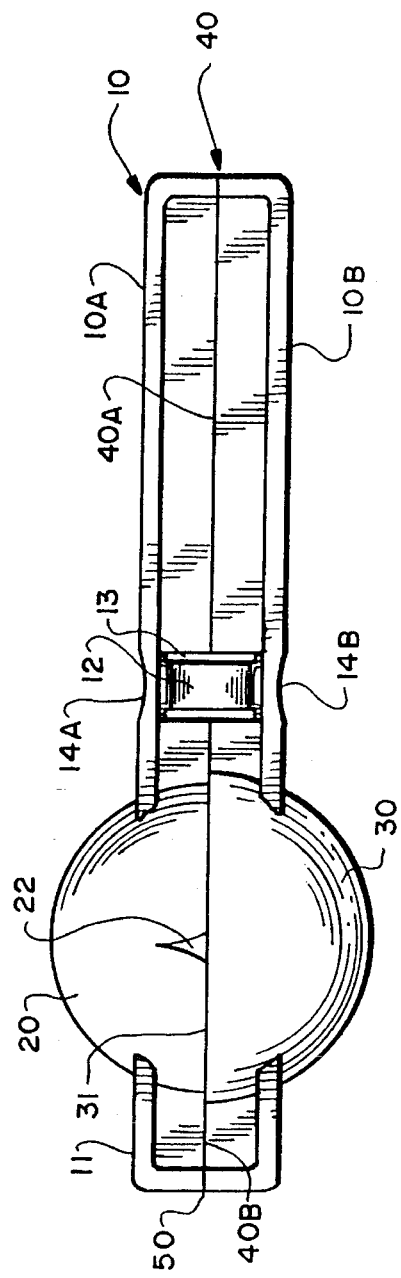
FIG. 4 is a bottom view of the embodiment of FIG. 1, with the spoon sections in the overlapping closed position of FIG. 3, with the opening at the apex of the V slit plainly visible.

Reference is now made to FIGS. 1, 2, 3, and 4, which illustrate pictorially the various elements of the preferred embodiment of the invention.

The preferred embodiment of the invention is a handtool used to facilitate the removal of a tick or similar parasite from the skin of a pet or person. It comprises a handle 10 to which is attached a pair of quadrispherical, or spoon-shaped sections 20 and 30, the outer diameter of section 20 being about the same size as the inner diameter of section 30.

The sections are hingedly attached at opposite ends by a living hinge 40 running through the centerline of the tool; hinge component 40A through handle 10, dividing handle 10 into left and right side components 10A and 10B, and hinge component 40B running through tab section 11 at the other end of spoon sections 20 and 30. This allows sections 20 and 30 to be rotated between an open, non-overlapping relative position and a closed, overlapping relative position.

The leading or mating edge 21 of the smaller diameter spoon section 20, incorporates a V-shaped slit 22, the mouth of which is closed by the leading edge 31 of section 30 as the two sections come together. The opening through slit 22 is progressively reduced in size as the sections further overlap. A mechanical stop 50 prevents the sections from overlapping far enough to close off slit 22 entirely. Slit 22 has tapered wall 23 to provide a thin, interfacing edge to the advancing section 30 as the slit closes, providing ample room for the tick's shoulders and body.

Handle components 10A and 10B incorporate opposing thumb and first finger locators 14A and 14B respectively, to facilitate a natural grip by either hand. The tool is spring loaded by spring 12 located in spring recess 13 within handle 10, to be held in a normally open position which is large enough to easily allow manual positioning of the tick removal tool over the body of a tick embedded in a host. Spring 12 is an integral, molded component of the tool.

A closing rotation of spoon sections 20 and 30 is manually actuated by the user by lightly pinching locators 14A and 14B, such that the tick body is encased within the bowl formed by the sections, it's neck confined within slit 22, while mechanical stop 50 prevents the tick's body from being severed from it's imbedded head. An agitant may be conveniently applied to the tick if desired, to encourage release from the host, although some sources report this may trigger a regurgitating reflex by the tick that may be more harmful to the wound and/or the host, due to further risk of infection.

The implement is held such that the handle is generally perpendicular to the view of the user. The natural grip places the thumb and forefinger close to the point of closure on the tick, for best control. There is no arm or wrist motion necessary for closure, once the tool is in position. The palm can be rested lightly on the host to steady the tool.

The round external shape of the bowl or spoon portion of the tool facilitates positioning it into a hairy area or into folds of skin. Only light compression by the thumb and forefinger is required to close the tool and trap the tick. The tick in the bowl of the tool is readily visible at all times to the user.

A gentle, persistent, lifting and twisting of the tick removal tool, using the palm of the hand resting on the subject for leverage and control, causes the tick to release from the skin and be thereby available for inspection to confirm removal of head and jaws, and release of the tick for appropriate disposal or medical analysis by allowing the tool to open to it's normal position.

A successful extraction requires a delicate touch; enough pressure to force the tick to release it's hold, but not so much as to tear the body from the embedded head. The normally open characteristic of the preferred embodiment of the subject invention requires a light but conscious closing effort which promotes a more sensitive effort by the user to extract the tick intact, as compared to normally closed devices.

I claim:

1. A tool for removing ticks and similar parasites, comprising a handle, two spoon-shaped sections, means by which said sections are hingedly attached on an axis parallel to said handle so as to be rotatable between an open position and a closely-fitting overlapping closed position, and a mechanical stop determining said closed position, the first of said sections having an open slit in one edge, said slit being first closed and then reduced in size by the second of said sections as said sections are rotated from said open position to said overlapping closed position.

2. The tool of claim 1, said tool configured with at least one spring configured to normally maintain said sections in said open position and resist rotation towards said overlapping closed position.

3. The tool of claim 1, said tool configured with at least one spring configured to normally maintain said sections in said overlapping closed position and resist rotation towards said open position.

4. The tool of claim 2, wall of said slit being tapered to provide a thin interfacing edge to said second of said sections in said overlapping closed position.

5. The tool of claim 2, said handle comprising left and right side components, each of said components attached to a respective said section and being rotatable therewith.

6. The tool of claim 5, said left and right side components incorporating opposing thumb and finger locators, said locators being interchangeably usable by left and right hands.

7. The tool of claim 6, said means by which said sections are hingedly attached comprising a centerline hinge connecting said left and right side components of said handle.

8. The tool of claim 7, said spring installed in a spring recess in said handle.

9. The tool of claim 7, wherein said left and right side components, said centerline hinge, and said spoon-shaped sections are produced as a one piece molding.

10. The tool of claim 7, wherein said left and right side components, said centerline hinge, said spoon-shaped sections, and said spring are produced as a one piece molding.

11. A tool for removing ticks and similar parasites, comprising a handle, two spoon-shaped sections, means by which said sections are hingedly attached on an axis parallel to said handle so as to be rotatable between an open position and a closely-fitting overlapping closed position, and a mechanical stop determining said closed position, the first of said sections having a slit in one edge, said slit being first closed and then reduced in size by the second of said sections as said sections are rotated from said open position to said overlapping closed position, said tool configured with at least one spring configured to normally maintain said sections in said open position and resist rotation towards said overlapping closed position, wall of said slit being tapered to provide a thin interfacing edge to said second of said sections in said overlapping closed position, said handle comprising left and right side components, each of said components attached to a respective said section and being rotatable therewith, said left and right side components incorporating opposing thumb and finger locators, said locators being interchangeably usable by left and right hands, said means by which said sections are hingedly attached comprising a centerline hinge connecting said left and right side components of said handle, said spring configured in a spring recess in said handle, wherein said left and right side components, said centerline hinge, said spoon-shaped sections, and said spring are produced as a one piece molding.

* * * * *